(12) United States Patent
Berhalter et al.

(10) Patent No.: US 6,927,260 B2
(45) Date of Patent: Aug. 9, 2005

(54) OPTIMIZATION OF HEAT REMOVAL IN A GAS-PHASE FLUIDIZED-BED PROCESS

(75) Inventors: Klaus Berhalter, Hale (GB); Walter Schicketanz, Frankenthal (DE); Gerard Duc, Mannheim (DE)

(73) Assignee: Basell Polyolefine GmbH (DE)

( * ) Notice: Subject to any disclaimer, the term of this patent is extended or adjusted under 35 U.S.C. 154(b) by 0 days.

(21) Appl. No.: 10/486,011

(22) PCT Filed: Aug. 7, 2002

(86) PCT No.: PCT/EP02/08832

§ 371 (c)(1),
(2), (4) Date: Feb. 5, 2004

(87) PCT Pub. No.: WO03/014169

PCT Pub. Date: Feb. 20, 2003

(65) Prior Publication Data

US 2004/0214968 A1 Oct. 28, 2004

(30) Foreign Application Priority Data

Aug. 10, 2001 (DE) .......................... 101 39 477

(51) Int. Cl.[7] ................................. C08F 2/34
(52) U.S. Cl. .......................... 526/67; 526/68; 526/90; 526/352; 526/901; 422/139; 208/416; 208/418
(58) Field of Search .................. 526/67, 68, 90, 526/352, 901; 422/139; 208/416, 418

(56) References Cited

U.S. PATENT DOCUMENTS 4,126,645 A 11/1978 Collins ..................... 260/677
4,577,047 A 3/1986 Hudson ..................... 585/260
5,804,677 A 9/1998 Chinh et al. ................ 526/68

FOREIGN PATENT DOCUMENTS

| EP | 0089691 A2 | 9/1983 | |
| EP | 0089691 B1 | 9/1983 | |
| EP | 0157584 | 10/1985 | |
| EP | 0853091 | 7/1998 | |
| EP | 1001001 | 5/2000 | |
| EP | 1001001 A1 * | 5/2000 | .......... C10G/57/02 |

* cited by examiner

Primary Examiner—William K. Cheung
(74) Attorney, Agent, or Firm—Connolly Bove Lodge & Hutz LLP

(57) ABSTRACT

A process for preparing polyethylene from "feed ethylene" comprises: a) a hydrogenation stage in which "feed ethylene" containing impurities or secondary components such as acetylene and ethane is reacted with hydrogen to remove the acetylene by catalytic hydrogenation to form ethylene and part of the ethylene is converted into ethane, and b) a polymerization stage in which the ethylene leaving stage a) is reacted in the gas phase in a fluidized-bed reactor to form polyethylene, where the fluidizing gas used comprises, on entering the reactor, ethene and from 20 to 70% by volume of ethane, based on the total volume of the fluidizing gas, possibly together with further components, where, in a), ethylene is converted in a targeted manner into ethane in addition to the ethane already present in the "feed ethylene" so that the concentration specified in b) results. An apparatus for carrying out the process is also provided. In the process claimed, ethane is used to increase the heat capacity of the fluidizing gas used.

8 Claims, 2 Drawing Sheets

OPTIMIZATION OF HEAT REMOVAL IN A GAS-PHASE FLUIDIZED-BED PROCESS

Figure 1:
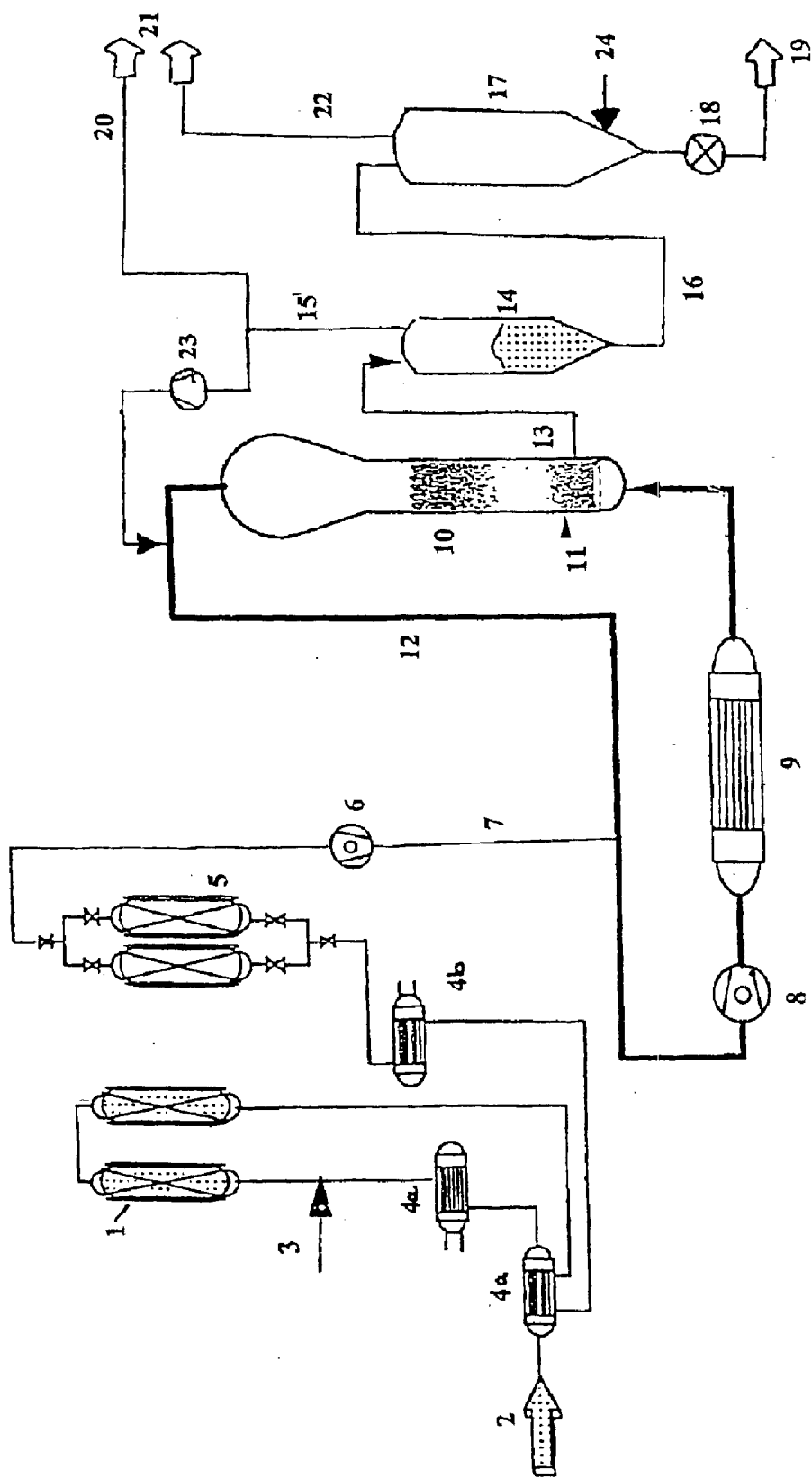

The invention relates to a process for preparing polyethylene from ethylene in the gas phase in a fluidized-bed reactor.

The polymerization of monomers in the gas phase to form polymers in a fluidized-bed reactor (fluidized-bed process) using catalysts is a widely used process, in particular for the polymerization of ethylene to polyethylene. Here, a fluidized bed is generated by passing gases (fluidizing gas) from below through finely divided material, in the case of the preparation of polyolefins, in particular polyethylene, generally polyolefin particles and catalyst, resting on a horizontal, perforated plate so as to produce, under particular flow conditions, a state in which the particles of the material in the fluidized bed are in continual, turbulent up-and-down motion and thus remain suspended to a substantial extent.

Compared to conventional processes, the use of the fluidized-bed process for the polymerization of ethylene offers a reduction in capital costs and a drastic reduction in energy consumption.

EP-A 0 853 091 relates to a process for the gas-phase polymerization of olefins in the presence of a catalyst system comprising a metallocene and a lower alkane, preferably n-butane, n-pentane, n-hexane or isobutane.

EP-B 0 157 584 relates to a process for the polymerization or copolymerization of α-olefins in a fluidized-bed reactor. According to the example, use is made of a fluidizing gas which comprises 42% by volume of ethylene, 40% by volume of hydrogen, 10% by volume of ethane and 8% by volume of nitrogen.

A decisive factor in achieving high space-time yields is the removal of the heat of reaction evolved in the strongly exothermic polymerization in the fluidized bed. Temperatures which are too high can not only lead to decomposition of the product or the catalyst but conglutination of the polymer particles during the polymerization can occur even at relatively low temperatures. Such conglutination can lead to formation of lumps in the reactor and result in a shutdown of the reactor.

The amount of polymer which can be prepared in a fluidized-bed reactor of a given size in a given time is thus directly dependent on the quantity of heat of reaction which can be removed. There are therefore a number of possible methods of removing the heat of polymerization in a fluidized-bed reactor.

A generally customary method is cooling the circulating gas stream leaving the reactor by means of heat exchangers outside the reactor and subsequently reintroducing the gas stream by means of compression. A disadvantage of this method is that the circulating gas stream which is necessary to take up the heat of polymerization has to be considerably greater than the gas stream actually necessary for maintaining the fluidized bed.

A further possible way of removing heat from the polymerization bed is increasing the proportion of monomer. However, this method is limited, depending on the activity of the catalyst, by increases in the monomer concentration in the gas space increasing the risk of deposit formation due to polymerization of fine dust deposits on the reactor wall and thus forcing shutdown.

EP-B 0 089 691 relates to a continuous process for preparing a polymer in a fluidized-bed reactor, in which process the unreacted circulating gas is partly or wholly cooled to a temperature below the dew point so as to form a two-phase mixture of gas and entrained liquid and is reintroduced into the reactor. Vaporization of the condensed material in the fluidized bed enables heat removal from the fluidized bed to be improved. This method allows a significant increase in heat removal from the fluidized bed, but suffers from the disadvantage that a considerable layout in engineering terms is required for purifying and introducing the liquid hydrocarbon components or for the separation of gas and condensable material.

The ethylene used is generally purified, i.e. polar components which act as catalyst poisons are removed. Furthermore, acetylenes which likewise adversely affect the catalyst activity are hydrogenated.

The ethylene fed to the reaction circuit to replace the monomer which has been converted into polyethylene and also to replace losses usually contains a relatively small proportion of ethane, with 0.1% by volume usually being aimed at as a maximum content (viz. "polymer grade" ethylene).

It is an object of the present invention to provide a further method of removing heat in a fluidized-bed process for the preparation of polyethylene from ethylene.

We have found that this object is achieved by a process for preparing polyethylene from "feed ethylene", which comprises:
a) a hydrogenation stage in which "feed ethylene" containing impurities or secondary components such as acetylene and ethane is reacted with hydrogen to remove the acetylene by catalytic hydrogenation to form ethylene and part of the ethylene is converted into ethane, and
b) a polymerization stage in which the ethylene leaving stage a) is reacted in the gas phase in a fluidized-bed reactor to form polyethylene, where the fluidizing gas used comprises, on entering the reactor, ethene and from 20 to 70% by volume of ethane, based on the total volume of the fluidizing gas, possibly together with further components, where the concentration specified in b) in addition to the ethane already present in the "feed ethylene" results from a targeted conversion of ethylene in a) into ethane and optionally/or a feed-stream of ethane added to the "feed ethylene".

For the purposes of the present invention, "feed ethylene" is the ethylene obtained in ethylene production in a steam cracker. This ethylene further comprises acetylene and ethane in a proportion of usually, for example, 5 ppm of acetylene and 0.1% by volume of ethane.

For the purposes of the present invention, fluidizing gas is the gas which is fed into the fluidized bed of the fluidized-bed reactor. It comprises reactive components, in the case of ethylene polymerization ethylene and, if desired, comonomers such as propylene, butylene, etc., partly reactive components such as hydrogen and components which are inert in the polymerization, e.g. nitrogen and ethane and possibly higher saturated hydrocarbons. The fluidizing gas serves firstly to fluidize the polymerization bed and secondly to remove the heat of reaction.

For the purposes of the present invention, circulating gas is the gas which leaves the fluidized-bed reactor after reaction over the polymerization catalyst. This gas, which contains less ethylene than the fluidizing gas as a result of the polymerization, is circulated and, usually after compression, cooling and addition of "feed ethylene" treated as described above, fed back into the reactor as fluidizing gas and/or removed fully or partly from the reactor.

The process of the present invention offers a series of advantages compared to the processes known from the prior art. Firstly, it offers a further opportunity of increasing heat removal from the polymerization bed and the reactor system. If the inerts consist largely of ethane, i.e. the nitrogen usually employed is largely replaced by ethane, and the addition of other inert components is restricted to the minimum required, it is possible to exploit the advantage that ethane has a higher volume (or molar) heat capacity than nitrogen. Better heat removal from the polymerization bed is achieved in this way, and the circulating gas can be cooled by a smaller temperature difference.

A further advantage of the process of the present invention is that ethane-"contaminated" ethylene can be used in the polymerization stage. In the hydrogenation stage a), acetylene present in the "feed ethylene" is hydrogenated to ethylene over a hydrogenation catalyst. In addition, ethane is generally formed at the same time. However, the separation of the ethane from the ethylene used is difficult, since ethylene and ethane have very similar boiling points. The polymerization of ethylene to polyethylene is usually carried out using ethylene having a purity of ≧99.9% ("polymer grade"). The process of the present invention makes it possible to use ethylene containing from 0.1 to 5% by volume of ethane, preferably from 0.2 to 0.6% by volume. This means that the process of the present invention allows a less complete separation of ethane from ethylene to be carried out, which results in cost savings in the preparation and purification of ethylene, for example in a steam cracker.

In addition to the ethane introduced via the "feed ethylene" stream, the concentration of ethane in the ethylene employed for the polymerization is, in the hydrogenation stage a), brought in a targeted manner to such a level that the desired ethane concentration in the circulating gas is reached and other inert gases are thus largely replaced by the ethane and this concentration is maintained in the circulating gas. It is also in the scope of the invention to use in addition to the ethane already present in the "feed ethylene" stream, a feed-stream of ethane. This "feed ethane" stream can be a direct cracker stream, in which case the "feed ethan" is preferably mixed with the "feed ethylene" before the purification section. Another source of "feed ethane" is the circulating gas. If the circulating gas is used as "feed ethane", this is preferably added via the ciculating gas line to which the "feed ethylene" or partly hydrogenated "feed ethylene" is usually added before entering the circulating compressor. It is also possible to mix the different ethane sources, e.g. a mixture of "feed ethane" from the cracker and/or the circulating gas and the hydrogenated "feed ethylene" stream.

The different ethane sources can also vary during the polymerisation process. In a preferred embodiment during start-up of the reactor the "feed ethane" from the cracker is used. Then on reaching steady state conditions the "feed ethane" from the circulating gas is used.

The different amount of components in the fluidizing gas, e.g. the amount of ethane and ethylene can be conveniently monitored by a gas chromatograph, which is usually connected to the circulating line just before or after the circulating gas compressor.

Before entering the reactor, the fluidizing gas comprises from 30 to 80% by volume of ethylene, from 20 to 70% by volume of ethane and possibly further components as e.g. comonomers, in particular from 0 to 10% by volume of nitrogen and from 0 to 5% by volume of hydrogen. The fluidizing gas preferably comprises from 50 to 65% by volume of ethylene, from 35 to 50% by volume of ethane, from 0 to 5% by volume of nitrogen, from 0 to 2% by volume of hydrogen, based on the total volume of the fluidizing gas, and possibly further components, e.g. from 0.1 to 6% by volume of hexene. Very particular preference is given to virtually all the nitrogen in the fluidizing gas being replaced by ethane.

The ethylene and any comonomers present in the fluidizing gas is/are converted into polyethylene in the fluidized-bed reactor. The polyethylene is discharged from the reactor, usually by periodic or continuous opening of one or more valves, and collected. Part of the gas present in the reactor is carried out together with the polyethylene (output stream). A major part of the output stream is returned to the circulating gas stream, while the other part of the output stream is discharged from the system. This results in a loss of inert gas (essentially ethane, nitrogen, hydrogen and possibly further components). This loss is replaced by the corresponding proportion of ethane in the ethylene from the hydrogenation stage.

Hydrogenation Stage a)

In the hydrogenation stage, the acetylene obtained in the preparation of ethylene, e.g. the acetylene present in the "crude ethylene" produced in a steam cracker, is hydrogenated, since acetylene would interfere in the polymerization of ethylene. In addition, ethylene is converted in a targeted manner into ethane so that the concentration of ethane in the fluidizing gas used in the subsequent polymerization stage is from 20 to 70% by volume, preferably from 35 to 50% by volume, based on the total volume of the fluidizing gas.

As hydrogenation catalysts, use is made of the catalysts customary for hydrogenation, for example catalysts based on platinum, palladium, rhodium or transition metals such as molybdenum, tungsten, chromium or iron, cobalt, copper and nickel, which can be used either individually or in admixture, generally applied to supports such as activated carbon, ceramics, etc. The hydrogenation is usually carried out at from 20 to 135° C., preferably from 90 to 95° C., particularly preferably from 92 to 95° C. The heat of hydrogenation obtained in the hydrogenation stage is preferably utilized for heating the "feed ethylene", which is advantageous for the starting and continuation of the hydrogenation.

The ethylene obtained is purified if necessary and introduced into the circulating gas which is fed to the fluidized-bed reactor.

Polymerization Stage b)

The polymerization stage is preferably carried out by passing the fluidizing gas through a fluidized bed comprising polyethylene particles and catalyst and cooling the gas leaving the fluidized bed and reintroducing it into the fluidized bed, with ethylene which has reacted being replaced by addition to the circulating gas or by direct introduction into the reactor and polyethylene being discharged from the reactor by periodic or continuous opening of valves.

The catalyst is generally introduced into the fluidized-bed reactor directly, either in pure form or by means of a gas, e.g. an inert gas, e.g. nitrogen, argon and/or ethane, or in a prepolymer. In a preferred embodiment, the catalyst is added by means of a gas, but without nitrogen, using a relatively unreactive, e.g hydrogen or inert hydrocarbon as carrier gas, preferably one having a very high concentration of ethane, preferably virtually only ethane. In a preferred embodiment ethane is used, especially preferred "feed ethane" from the cracker, which is preferably purified before the contact with the catalyst. When introduced in this way, the catalyst is preferably introduced in powder form.

Catalysts used are usually compounds such as transition metal compounds on a support. Preference is given to titanium, zirconium and chromium compounds. Examples of suitable catalysts are Ziegler and Phillips catalysts or metallocenes of transition metals of group 4, 5 and 6, preferably titanium, zirconium, hafnium and chromium, which comprise one or two substituted, unsubstituted or condensed cyclopentadienyl systems. It is also possible to use a mixture of various catalysts in the process of the present invention.

The polymerization temperatures are usually from 70 to 125° C., preferably from 85 to 120° C., particularly preferably from 90 to 115° C. The polymerization pressure is generally from 10 to 40 bar, preferably from 20 to 30 bar, particularly preferably from 20 to 25 bar.

The gas leaving the fluidized bed (circulating gas) is cooled, generally by means of an external heat exchanger, and fed back into the fluidized bed, with a compressor serving to restore the pressure. The reacted monomer(s) is/are replaced by the ethylene purified in the hydrogenation stage. This is generally added to the circulating gas, but can also be fed directly into the reactor.

Polyethylene obtained is discharged directly from the reactor, usually by periodic or continuous opening of one or more valves into a region of lower pressure. The polyethylene is carried out through the open valves by the gas present in the reactor (output stream) as a result of the pressure gradient. The polyethylene is collected in an output vessel and separated from the output stream in one or more stages. Part of the output stream can be returned via a return gas compressor to the circulating gas stream, while the other part of the output stream can be discharged from the system and replaced by the corresponding amount of ethane in the ethylene from the hydrogenation stage a) or by addition of fresh inert gas to the circulating gas stream. The part of the output stream which is discharged is preferably replaced entirely by the corresponding amount of ethane in the ethylene from the hydrogenation stage a) (additionally tolerable ethane concentration).

The considerations applying to the additionally tolerable ethane concentration (specification) are described below by way of example.

a) (cf. FIG. 1)

The polyethylene carried out in the output stream 13 (output stream I) goes into a vessel 14 (separator I) at an intermediate pressure of generally from 1.5 to 10 bar, preferably from 2 to 8 bar, particularly preferably from 3 to 6 bar. In this separator I, the pulverulent polyethylene separates from the major part of the gas of the output stream. This proportion leaves the vessel 14 as stream 15, after which, if desired, a substream 20 is discharged from the reaction system, e.g. completely off the reaction system. The pulverulent polyethylene is in turn discharged from the separator I by periodic or continuous opening of one or more valves as stream 16 and goes into the vessel 17 (separator II) which is operated at a pressure of generally from 1.0 to 8 bar, preferably from 1.1 to 3 bar, particularly preferably from 1.1 to 1.5 bar. The polyethylene discharged from the separator I carries with it a proportion of gas, viz. the output stream II (cf. FIG. 1). The only stream leaving the reaction circuit is thus the stream 16 (output stream II) going into the separator II, 17, if one disregards diffuse losses and possible deliberate purge streams, e.g. the purge stream 20. In the separator II, the major part of the output stream II is separated from the polyethylene. If a gas, e.g. nitrogen, is additionally introduced into this vessel for flushing purposes (stream 24) and/or sealing purposes or it gets into this vessel in other ways, it is generally not economically feasible to separate the hydrocarbons from this stream and return them to the reaction system. This off gas (stream 22) is usually burnt. The maximum ethane concentration in the "feed ethylene" is then derived from the following balance: the output stream II has virtually the same concentration of the individual components as the gas in the reactor. The mass flow of ethane leaving the reaction system, i.e. output stream times concentration of ethane (now concentration by weight), is equal to the inflow of ethane, i.e. "feed ethylene" stream times maximum possible ethane concentration (now concentration by weight). (The other gas and inert gas streams introduced into the reaction system have been disregarded in the interests of simplicity.)

EXAMPLE

Figure 2:
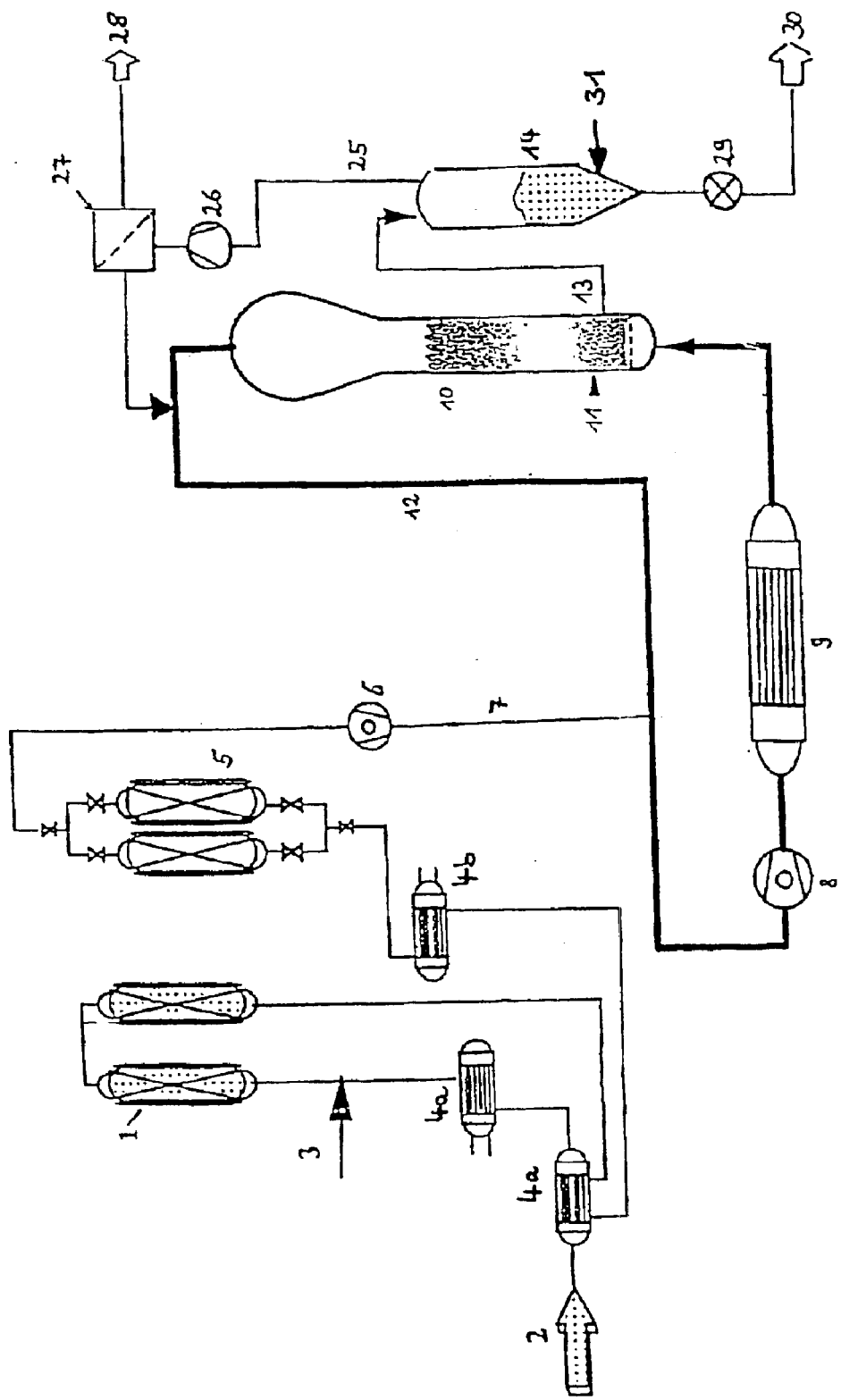

The nitrogen concentration of about 50% by volume in the reactor is to be replaced completely by ethane. If the output stream II amounts to about 8% % by volume of the polyethylene stream produced, the "feed ethylene" stream can contain a maximum of about 4% by volume of ethane.

b) (cf. FIG. 2)

The polyethylene is carried out in the output stream directly into a vessel 14 whose pressure is close to atmospheric pressure, in general from 1 to 8 bar, preferably from 1.1 to 3 bar, particularly preferably from 1.1 to 1.5 bar. In addition, nitrogen and/or a number of essentially inert gases, preferably ethane are introduced into this vessel, e.g. for flushing purposes or for sealing purposes (FIG. 2).

The polyethylene (together with a certain proportion of gas) and the stream 25 which now further comprises nitrogen or other components leave this vessel. The gas stream 25 is separated into light, inert constituents, i.e. mostly nitrogen, and heavy constituents, mostly ethene and ethane. The latter are returned to the reaction system (circulating gas 12).

Depending on the efficiency of the separation, there is a loss of ethane; if appropriate, a small stream or a number of streams of the heavy constituents is discharged from the system (purge or bleed stream).

If ethane is used for flushing no seperator unit is necessary. The gas stream 25 can then be returned to the cracker for destination or returned to the reaction system.

The maximum additionally tolerable ethane concentration in the "feed ethylene" is again derived via the mass balance.

The permissible ethane concentration in the fresh ethylene can thus, when all the nitrogen is replaced by ethane, increase considerably, which allows a significant reduction in the fresh ethylene price. The energy consumption in the ethylene distillation drops significantly. Nitrogen or alternatively ethane or another hydrocarbon may still be required for feeding in the catalyst.

If the ethane concentration in the ethylene is too low to replace all the losses of inert gas, fresh ethane in a more or less high concentration can additionally be added to the circulating gas stream, e.g. via the introduction of catalyst or independently therefrom.

The polyethylene obtained is passed to further processing steps such as a final degassing by means of flushing gas and/or pelletization.

The replacement of nitrogen by ethane in the inert gas component enables, owing to the higher heat capacity of ethane, improved heat removal from the reactor system to be achieved. This effect is particularly pronounced at a high inert gas content. The inert gas content in the fluidizing gas is therefore from 20 to 70% by volume, preferably from 35 to 50% by volume. The proportion of the total volume of the inert gas made up by ethane is from 66 to 100% by volume, preferably from 92 to 100% by volume. The higher heat capacity of ethane compared to nitrogen makes, in the case of replacement of part of the nitrogen by ethane, a higher temperature difference available for cooling of the circulating gas at the same reactor outlet temperature. Thus, the capacity of the reactor can generally be increased by 10–35% compared to the usual capacity.

BRIEF DESCRIPTIONS OF THE DRAWINGS

FIG. 1 of the accompanying drawing shows an apparatus for carrying out the process of the present invention. The reference numerals in the figure have the following meanings:

1 Hydrogenation reactor
2 Feed line for ethylene
3 Feed line for hydrogen
4a Heat exchanger (preheater)
4b Heat exchanger (cooler)
5 Downstream purification stages
6 Ethylene compressor
7 Line from hydrogenation reactor-to circulating gas line
8 Circulating gas compressor
9 Circulating gas cooling
10 Fluidized-bed reactor
11 Inlet for the catalyst
12 Circulating gas line
13 Outlet for polyethylene (output stream I)
14 Output vessel (separator I)
15 Line to a return gas compressor
16 Output stream II
17 Separator II
18 Discharge device, e.g. cellular wheel
19 Polyethylene outlet
20 Possible purge stream
21 Offgases
22 Offgas
23 Return gas compressor
24 Flushing gas inlet, e.g. for nitrogen FIG. 2 of the accompanying drawing shows an apparatus for carrying out the process of the present invention. The reference numerals in the figure have the following meanings:

1 Hydrogenation reactor
2 Feed line for ethylene
3 Feed line for hydrogen
4a Heat exchanger (preheater, operating for example by regenerative heat exchange)
4b Heat exchanger (cooler)
5 Downstream purification stages
6 Ethylene compressor
7 Line from hydrogenation reactor to circulating gas line
8 Circulating gas compressor
9 Circulating gas cooling
10 Fluidized-bed reactor
11 Inlet for the catalyst
12 Circulating gas line
13 Outlet for polyethylene (output stream)
14 Output vessel (separator)
25 Line to a return gas compressor
26 Return gas compressor
27 Separation unit for separating off nitrogen
28 Offgases
29 Discharge device, e.g. cellular wheel
30 Polyethylene outlet
31 Flushing gas inlet, e.g. for nitrogen The present invention further provides an apparatus (FIG. 1) for carrying out the process of the present invention, comprising a) a hydrogenation reactor 1 which has a feed line for ethylene 2 and a feed line for hydrogen 3, and
b) a fluidized-bed reactor 10 whose bottom and top are connected to a circulating gas line 12 which has a circulating gas cooler 9, where the fluidized-bed reactor 10 has an inlet for the catalyst 11 and an outlet 13 for polyethylene which is collected in a first separator 14 in which a substream of the gas carried out from the fluidized-bed reactor 10 separates from the pulverulent polyethylene and this gas is conveyed via a line 15, with a substream of the gas being discharged via a line 20 if desired, and via a compressor 23 and, if desired, conveyed via the circulating gas line 12 back into the fluidized-bed reactor 10, and the first separator 14 is connected via a further line 16 to a second separator 17 in which the polyethylene is separated from further gas carried out from the separator 14 and the polyethylene is taken off via a discharge device 18 and a line 19 while the gas which has been separated off leaves the second separator 17 via a line 22, together with any gas introduced via line 24 or in another way, where the outlet of the hydrogenation reactor 1 is connected via a line 7 to the fluidized-bed reactor 10 or the circulating gas line 12.

In a further embodiment of the process of the present invention, the apparatus (FIG. 2) for carrying out the process of the present invention has the following features:

a) a hydrogenation reactor 1 which has a feed line for ethylene 2 and a feed line for hydrogen 3, and
b) a fluidized-bed reactor 10 whose bottom and top are connected to a circulating gas line 12 which has a circulating gas cooler 9, where the fluidized-bed reactor 10 has an inlet for the catalyst 11 and an outlet 13 for polyethylene formed which is collected in a separator 14 which is connected via a line 25 to the fluidized-bed reactor 10 or the circulating gas line 12, where a substream separated off in the separator 14 from the gas which is carried out from the fluidized-bed reactor 10 is conveyed via a compressor 26 and, if appropriate, a separation unit 27 and, if appropriate, via the circulating gas line 12 back into the fluidized-bed reactor 10, with a substream being, particularly if it has a high nitrogen content, discharged from the system via a line 28 together with any gas introduced via line 31 or in another way, and the polyethylene is taken off via a discharge device 29 and a line 30, where the outlet of the hydrogenation reactor 1 is connected via a line 7 to the circulating gas line 12.

The outlet of the hydrogenation reactor 1 is preferably connected to columns 5 for further purifying the hydrogenation gas before the ethylene is introduced into the circulating gas line 12.

The feed lines for ethylene 2 and for hydrogen 3 can be combined as a joint feed line which is connected to the hydrogenation reactor 1.

The present invention further provides for the use of ethane in the process of the present invention for increasing the heat capacity of the fluidizing gas used.

The following example illustrates the invention.

EXAMPLE

The following table shows the specific heat capacities of various fluidizing gas compositions.

| Ethylene [% by vol.] | $N_2$ [% by vol.] | Hexane [% by vol.] | Ethane [% by vol.] | Specific heat capacity kJ/kgK (100° C.) |
|---|---|---|---|---|
| 46.5 | 50 | 3.5 | — | 1.48 |
| 46.5 | — | 3.5 | 50 | 1.96 |
| 85 | 10 | 5 | — | 1.79 |
| 85 | — | 5 | 10 | 1.88 |

What is claimed is:

1. A process for preparing polyethylene from "feed ethylene", which comprises:
   a) a hydrogenation stage in which "feed ethylene" containing impurities or secondary components such as acetylene and ethane is reacted with hydrogen to remove the acetylene by catalytic hydrogenation to form ethylene and part of the ethylene is converted into ethane, and
   b) a polymerization stage in which the ethylene leaving stage a) is reacted in the gas phase in a fluidized-bed reactor to form polyethylene, where the fluidizing gas used comprises, on entering the reactor, ethene and from 20 to 70% by volume of ethane, based on the total volume of the fluidizing gas, possibly together with further components, where the concentration specified in b) in addition to the ethane already present in the "feed ethylene" results from a targeted conversion of ethylene in a) into ethane and optionally/or a feed-stream of ethane added to the "feed ethylene", and wherein the fluidized gas leaving the reactor in stage b) is cooled and recycled directly back to the reactor.

2. A process for preparing polyethylene from "feed ethylene", which comprises:
   a) a hydrogenation stage in which "feed ethylene" containing impurities or secondary components such as acetylene and ethane is reacted with hydrogen to remove the acetylene by catalytic hydrogenation to form ethylene and part of the ethylene is converted into ethane, and
   b) a polymerization stage in which the ethylene leaving stage a) is reacted in the gas phase in a fluidized-bed reactor to form polyethylene, where the fluidizing gas used comprises, on entering the reactor, ethene and from 20 to 70% by volume of ethane, based on the total volume of the fluidizing gas, possibly together with further components.

where the concentration specified in b) in addition to the ethane already present in the "feed ethylene" results from a targeted conversion of ethylene in a) into ethane and optionally/or a feed-stream of ethane added to the "feed ethylene", and
   wherein the fluidizing gas before entry into the fluidized-bed reactor comprises from 50 to 65% by volume of ethylene, from 35 to 50% by volume of ethane, from 0 to 1% by volume of nitrogen, from 0 to 10% by volume of hydrogen, based on the total volume of the fluidizing gas, and possibly further components.

3. A process as claimed in claim 1, wherein the heat of hydrogenation obtained in the hydrogenation stage a) is utilized for heating the "feed ethylene".

4. A process as claimed in claim 1, wherein, in the polymerization stage b), the fluidizing gas is passed through a fluidized bed comprising polyolefin particles and catalyst and the gas leaving the fluidized bed is cooled and fed back into the fluidized bed, with ethylene which has reacted being replaced by addition to the circulating gas or by direct introduction into the reactor and polyethylene being discharged from the reactor by periodic or continuous opening of valves.

5. A process as claimed in claim 1, wherein the catalysts used in stage b) comprise transition metal compounds on a support.

6. An apparatus for preparing polyethylene from feed ethylene comprising:
   a) a hydrogenation reactor having a feed line for ethylene and a feed line for hydrogen, and
   b) a fluidized-bed reactor having a bottom and top connected to a circulating gas line which has a circulating gas cooler, where the fluidized-bed reactor has an inlet for a catalyst and an outlet for polyethylene which is collected in a first separator in which a substream of the gas carried out from the fluidized-bed reactor separates from pulverulent polyethylene and where the gas is conveyed via a first line, with a substream of the gas being conveyed via the circulating gas line back into the fluidized-bed reactor, and the first separator being connected via a second line to a second separator in which the polyethylene is separated from further gas carried out from the first separator, the polyethylene being taken off via a discharge device and a third line while the gas which has been separated off leaves the second separator via a fourth line, where outlet of the hydrogenation reactor is connected via a fifth line to the fluidized-bed reactor or the circulating gas line.

7. An apparatus for preparing polyethylene from feed ethylene comprising:
   a) a hydrogenation reactor having a feed line for ethylene and a feed line for hydrogen, and
   b) a fluidized-bed reactor having a bottom and top are connected to a circulating gas line which has a circulating gas cooler, where the fluidized-bed reactor has an inlet for a catalyst and an outlet for polyethylene formed which is collected in a separator which is connected via a line to the fluidized-bed reactor or the circulating gas line, where a substream separated off in the separator of the gas which is carried out from the fluidized-bed reactor is conveyed via a compressor back into the fluidized-bed reactor, with a substream being, discharged from the system via a first discharge line, and the polyethylene is taken off via a discharge device and a line, where an outlet of the hydrogenation reactor is connected via a line to the circulating gas line.

8. An apparatus as claimed in claim 6, wherein the outlet of the hydrogenation reactor is connected to columns for further purifying the hydrogenation gas.

* * * * *

UNITED STATES PATENT AND TRADEMARK OFFICE
CERTIFICATE OF CORRECTION

PATENT NO. : 6,927,260 B2
DATED : August 9, 2005
INVENTOR(S) : Klaus Berhalter et al.

It is certified that error appears in the above-identified patent and that said Letters Patent is hereby corrected as shown below:

Column 10,
Line 36, insert -- an -- after "where".
Line 54, delete "," after "being".
Line 56, insert -- second discharge -- after "a".

Signed and Sealed this

Eleventh Day of October, 2005

JON W. DUDAS
*Director of the United States Patent and Trademark Office*